US010590540B2

(12) United States Patent
Akaike et al.

(10) Patent No.: US 10,590,540 B2
(45) Date of Patent: Mar. 17, 2020

(54) SILVER-COATED PARTICLE AND METHOD OF PRODUCING SAME

(71) Applicant: MITSUBISHI MATERIALS CORPORATION, Tokyo (JP)

(72) Inventors: Hiroto Akaike, Naka (JP); Kazuhiko Yamasaki, Naka (JP)

(73) Assignee: MITSUBISHI MATERIALS CORPORATION, Tokyo (JP)

(*) Notice: Subject to any disclaimer, the term of this patent is extended or adjusted under 35 U.S.C. 154(b) by 250 days.

(21) Appl. No.: 15/545,861

(22) PCT Filed: Jan. 18, 2016

(86) PCT No.: PCT/JP2016/051303
§ 371 (c)(1),
(2) Date: Jul. 24, 2017

(87) PCT Pub. No.: WO2016/121558
PCT Pub. Date: Aug. 4, 2016

(65) Prior Publication Data
US 2018/0016679 A1 Jan. 18, 2018

(30) Foreign Application Priority Data

Jan. 28, 2015 (JP) ................. 2015-013984
Dec. 15, 2015 (JP) ................. 2015-244052

(51) Int. Cl.
*C23C 18/44* (2006.01)
*C23C 18/16* (2006.01)
*C23C 18/28* (2006.01)
*H01B 1/02* (2006.01)
*G01N 23/20* (2018.01)
*G01N 23/207* (2018.01)
*H01B 5/00* (2006.01)
*H01B 13/00* (2006.01)

(52) U.S. Cl.
CPC ........... *C23C 18/28* (2013.01); *C23C 18/166* (2013.01); *C23C 18/168* (2013.01); *C23C 18/1641* (2013.01); *C23C 18/1683* (2013.01); *C23C 18/1692* (2013.01); *C23C 18/285* (2013.01); *C23C 18/44* (2013.01); *G01N 23/20* (2013.01); *G01N 23/207* (2013.01); *H01B 1/02* (2013.01); *H01B 5/00* (2013.01); *H01B 13/00* (2013.01)

(58) Field of Classification Search
CPC .................... C23C 18/44; C23C 18/1641
See application file for complete search history.

(56) References Cited

U.S. PATENT DOCUMENTS

| | | | | |
|---|---|---|---|---|
| 3,632,435 A | * | 1/1972 | Eriksson | ............... H05K 3/182 427/98.1 |
| 2005/0127536 A1 | | 6/2005 | Totokawa et al. | |
| 2007/0075299 A1 | | 4/2007 | Ninomiya et al. | |
| 2007/0269603 A1 | | 11/2007 | Kubota | |
| 2008/0206567 A1 | * | 8/2008 | Min | .................... C23C 18/1635 428/404 |
| 2013/0140501 A1 | * | 6/2013 | Nakabayashi | ...... C23C 18/1641 252/514 |

FOREIGN PATENT DOCUMENTS

| | | |
|---|---|---|
| CN | 1416986 A | 5/2003 |
| CN | 102206818 A | 10/2011 |
| CN | 103814098 A | 5/2014 |
| EP | 2669344 A1 | 12/2013 |
| JP | 59-035433 B | 8/1984 |
| JP | 59-043521 B | 10/1984 |
| JP | 02-125881 A | 5/1990 |
| JP | 04-097912 A | 3/1992 |
| JP | 08-311655 A | 11/1996 |
| JP | 10-330948 A | 12/1998 |
| JP | 11-039937 A | 2/1999 |
| JP | 2012-256580 A | 12/2012 |
| WO | 2006/018995 A1 | 2/2006 |
| WO | 2009/054371 A1 | 4/2009 |
| WO | 2010/035708 A1 | 4/2010 |
| WO | 2012/023566 A1 | 2/2012 |

OTHER PUBLICATIONS

Machine Translation of JPH1139937A. Retrieved from google patents on Jun. 24, 2019 from https://patents.google.com/patent/JPH1139937A/en?oq=JP11-39937 (Year: 1997).*
Machine Translation of CN1416986. Retrieved from google patents on Jun. 24, 2019 from https://patents.google.com/patent/CN1416986A/en?oq=CN1416986 (Year: 2002).*
Supplementary European Search Report dated Aug. 23, 2018, issued for the European patent application No. 16743162.6.
International Search Report dated Mar. 29, 2016, issued for PCT/JP2016/051303 and English translation thereof.
Office Action dated Jul. 3, 2018, issued for the Chinese patent application No. 201680007251.X and a partial English translation of the Search Report.

* cited by examiner

Primary Examiner — Matthew E. Hoban
(74) Attorney, Agent, or Firm — Locke Lord LLP

(57) ABSTRACT

A silver-coated particle (P1) is provided. The silver-coated particle (P1) includes a core particle (2) made of a resin particle or an inorganic particle and a silver coating layer (1) formed on a surface of the core particle (2), wherein, an amount of silver contained in the silver coating layer (1) is 5 to 90 parts by mass with respect to 100 parts of the silver-coated particle (P1), a crystallite diameter of the silver, which is calculated from a diffraction line obtained by filling a sample holder belonging to an X-ray diffraction apparatus with the silver-coated particle (P1); and irradiating X-ray in a range of $2\theta/\theta=30$ to 120 deg., is in a range of 35 nm to 200 nm.

9 Claims, 1 Drawing Sheet

SILVER-COATED PARTICLE AND METHOD OF PRODUCING SAME

TECHNICAL FIELD OF THE INVENTION

The present invention relates to silver-coated particles suitable as conductive fillers contained in a conductive adhesive, a conductive film, and a conductive spacer and a method for producing the same. More specifically, the present invention relates to silver particles, in which cracking or fracturing of the silver coating layer; or peeling of the silver coating layer from the core particle hardly occurs. In addition, the conductivity of the conductive adhesive or the like can be improved Priority is claimed on: Japanese Patent Application No. 2015-013984, filed Jan. 28, 2015; and Japanese Patent Application No. 2015-244052, filed Dec. 15, 2015, the contents of which are incorporated herein by reference.

BACKGROUND OF THE INVENTION

Conductive adhesives have been studied as various substitute materials for the lead solder. Conductive adhesive is a mixture of resin and metal conductive particles, and typical examples are conductive paste and conductive ink. These conductive paste and conductive ink are superior in workability such as: stress absorption; low temperature mounting; micro pitch conduction; insulation; and not requiring use of the flux. Accordingly, these conductive paste and ink have been used for electrode connection of liquid crystal display, touch panel substrate, keyboard and the like. In order to make such a conductive paste and a conductive ink easier to use, metal coated resin particles in which metal particles are coated on core particles of resin particles as conductive particles have been developed. These metallic coated resin particles have the merit of reducing manufacturing cost and weight. As metallic coated resin particles, a conductive electroless plating powder, in which nickel is electrolessly plated on core particles of resin particles and gold is coated on the upper surface of the core particles of the metal particles, is disclosed (for example, refer Patent Literature 1 (PTL 1)). It is interpreted that the high conductivity performance is obtained since the Ni or Ni—Au coating which is the plating layer is strongly adhered to the resin particle which is the core particle in this conductive electroless plating powder. On the other hand, a silver-coated spherical resin is disclosed (for example, refer Patent Literature 2 (PTL 2)). The silver-coated spherical resin disclosed in PTL 2 has: a core particle of a spherical resin; a tin absorbing layer provided on the surface of the core particle; and silver coated on the surface of the tin absorbing layer. The amount of silver with respect to 100 parts by mass of the silver-coated spherical resin is 5 to 80 parts by mass in the silver-coated spherical resin disclosed in PTL 2. In addition, the crystallite diameter of the silver measured by the X-ray diffraction method is in the range of 18 nm to 24 nm. In the silver-coated spherical resin, the adhesiveness of the silver coating is increased: by performing a catalyzing treatment to the core particle of the spherical resin by tin; and then by performing electroless silver plating

RELATED ART DOCUMENTS

Patent Literature

PTL 1: Japanese Unexamined Patent Application, Second Publication No. H08-311655 (A) (Claim 1, paragraphs [0015] and [0016])
PTL 2: WO2012/023566 (A) (Claim 1)

SUMMARY OF THE INVENTION

Problems to be Solved by the Present Invention

In the method of PTL 1, in the case where the Ni—Au multi coating layer is formed on the core particle of the resin particle, the adhesiveness of the core particle of the resin particle to gold is increased by performing electroless gold plating after performing electroless nickel plating on the core particle of the resin particle. However, the nickel plating and the gold plating need to be performed separately in this method; and the plating treatment is cumbersome. Moreover, additional materials, substrates, and times for the treatments are needed. On the other hand, in the method of PTL 2, the adhesiveness is increased by densifying the silver coating by controlling the crystallite diameter to a low value of 18 nm to 24 nm, by performing electroless silver plating after providing the tin absorbing layer on the surface of the core particle of the spherical resin with the pretreatment by tin. However, in the coated spherical resin obtained by the method of PTL 2, the strength of the coating is not sufficient due to the small crystallite diameter. Thus, for example, when a high shear force is applied to the mixture of the core particles of the silver-coated spherical resin and the binder resin in order to prepare a conductive adhesive, cracking or fracturing occurs due to the intergranular fracture. Accordingly, there is a possibility that peeling of the silver coating layer from the core particle occurs because of the cracking or fracturing; and the conductivity of the conductive adhesive is reduced. Also, in the case of an anisotropic conductive adhesive, the peeled plating piece becomes a foreign body and enters into the gap that is supposed to be insulated originally, possibly causing a malfunction.

The object of the present invention is to provide a silver-coated particle, in which cracking or fracturing of the silver coating layer due to the intergranular fracture or peeling of the silver coating layer from the core particle hardly occurs; and the conductivity of the conductive adhesive or the like can be improved, when a shear force is applied to the mixture of the silver-coated core particles and the binder resin in order to prepare a conductive adhesive. In addition, a method of producing the above-described silver-coated particle is provided.

Means to Solving the Problems

The first aspect of the present invention is a silver-coated particle including a core particle made of a resin particle or an inorganic particle and a silver coating layer formed on a surface of the core particle, wherein, an amount of silver contained in the silver coating layer is 5 to 90 parts by mass with respect to 100 parts of the silver-coated particle, a crystallite diameter of the silver, which is calculated from a diffraction line obtained by filling a sample holder belonging to an X-ray diffraction apparatus with the silver-coated particle; and irradiating X-ray in a range of $2\theta/\theta=30$ to 120 deg., is in a range of 35 nm to 200 nm.

In the silver-coated particle of the first aspect of the present invention, since its crystallite diameter measured by the predetermined X-ray diffraction method is as large as 35 nm to 200 nm, the silver-coated particle has excellent coatability of the silver coating layer on the core particle, adhesiveness and film strength. As a result, even if a high shearing force is applied to the mixture of the silver-coated core particles and the binder resin in order to prepare a conductive adhesive or the like using the silver-coated particles, cracking or fracturing on the silver coating layer due to the intergranular fracture; or peeling of the silver coating layer from the core particle hardly occurs; and the conductivity of the conductive adhesive or the like can be improved.

The second aspect of the present invention is a method of producing a silver-coated particle including the steps of:

forming a tin absorbing layer on a surface of a core particle by adding the core particle made of a resin particle or an inorganic particle to an aqueous solution of a tin compound;

preparing a silver-coated particle precursor, which contains a silver coating layer on the surface of the core particle, by performing electroless plating on the tin absorbing layer, which is formed on the surface of the core particle, by using a reducing agent; and setting a crystallite diameter of the silver, which is measured by X-ray diffraction method, to 35 nm to 200 nm by sintering silver constituting the silver coating layer by heat treating the silver-coated particle precursor at: a temperature of 100° C. or more and less than 250° C. in an air after water-washing and drying the silver-coated particle precursor; or a temperature of 100° C. or more and less than 250° C. in water immediately after water-washing the silver-coated particle precursor, for 0.5 to 10 hours.

In the method of producing the silver-coated particle of the second aspect of the present invention, the silver-coated particle precursor is prepared; and the crystallites are sintered in the silver coating layer by heat treating the silver-coated particle precursor at: a temperature of 100° C. or more and less than 250° C. in an air after water-washing and drying the silver-coated particle precursor; or a temperature of 100° C. or more and less than 250° C. in water immediately after water-washing the silver-coated particle precursor, for 0.5 to 10 hours. Because of this, the crystallite diameter of silver is increased; and the degree of crystallinity is increased. Accordingly, the range of the crystallite diameter measured by the X-ray diffraction method becomes 25 nm to 200 nm. As a result, the silver coating layer coats the core particle more evenly by the heat treatment and adheres to the core particle more reliably. Therefore, a silver-coated particle having a higher conductivity can be obtained.

The third aspect of the present invention is a method of producing a conductive adhesive by mixing the silver-coated particle according to the first aspect and a binder resin.

The conductive adhesive produced by the method of the third aspect of the present invention has excellent conductivity.

The fourth aspect of the present invention is a method of producing a conductive film by applying a resin composition, which is prepared by mixing the silver surface-coated particle according to the first aspect and a binder resin, on a surface of a support film.

The conductive adhesive film produced by the method of the fourth aspect of the present invention has excellent conductivity.

The fifth aspect of the present invention is a method of producing a conductive spacer by pasting two substrate plates after applying a resin composition, which is prepared by mixing the silver surface-coated particle according to the first aspect and a binder resin, on one or both surfaces of the two substrate plates.

The conductive space produced by the method of the fifth aspect of the present invention has excellent conductivity.

Effects of the Invention

A silver-coated particle and a method of producing the silver-coated partible are provided. In the silver-coated particle, cracking or fracturing of the silver coating layer or peeling of the silver coating layer from the core particle hardly occurs; and the conductivity of the conductive adhesive or the like is improved, when a shear force is applied to the mixture of the core particles and the binder resin in order to prepare a conductive adhesive.

DETAILED DESCRIPTION OF THE INVENTION

Figure 1:
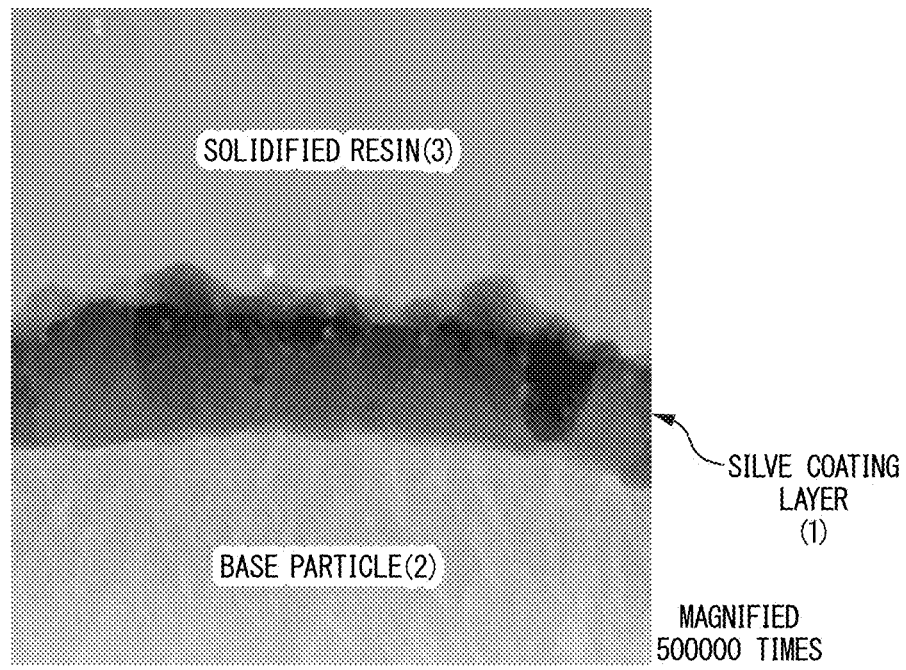
FIG. 1 shows a TEM image (magnification of 500,000 times) of a cross section of a silver coating layer of silver-coated particles P1 of Example 2. The core particle 2 and the silver coating layer 1 of the silver-coated particle P1 of the present invention are shown with the solidified resin 3.

Next, embodiments for carrying out the present invention will be described.

[Silver-Coated Particle]

The silver-coated particle P1 of the present embodiment includes the core particle 2 (base particle) and the silver coating layer 1 formed on the surface of the core particle 2. The amount of silver contained in the silver coating layer 1 is 5 to 90 parts by mass with respect to 100 parts by mass of the silver-coated particle. The crystallite diameter of the silver, which is calculated from the diffraction line obtained by filling the sample holder belonging to the X-ray diffraction apparatus with the silver-coated particles; and irradiating X-ray in the range of 2θ/θ=30 to 120 deg., is in the range of 35 nm to 200 nm, preferably in the range of 40 nm to 80 nm. The silver coating layer coats the core particle 2 with no gap. If the crystallite diameter of silver is less than 35 nm, the silver coating layer 1 does not cover the core particle 2 with no gap, and the coatability, adhesiveness and film strength of the silver coating layer 1 to the core particle 2 becomes inferior. If it exceeds 200 nm, the silver coating layer 1 shrinks due to over-sintering during production, the silver aggregates on the core particle 2, the coverage of the silver coating layer 1 tends to decrease. In addition, in the case where the core particle 2 is resin particle, the appearance of the silver-coated particle P1 is deteriorated; and it is possible that the silver coating layer 1 is peeled off due to deformation thereof.

[Method of Producing the Silver-Coated Particle]

The method of producing the silver-coated particle of the present embodiment includes: the steps of forming the tin absorbing layer on the surface of the core particle 2 by adding the core particle 2 to the aqueous solution of the tin compound warmed at 25° C. to 45° C.; preparing the silver-coated particle precursor, which contains the silver coating layer 1 on the surface of the core particle 2, by performing electroless plating on the tin absorbing layer, which is formed on the surface of the core particle 2, by using a reducing agent; and heat treating the silver-coated particle precursor at: a temperature of 100° C. or more and less than 250° C. in an air after water-washing and drying the silver-coated particle precursor; or a temperature of 100° C.

or more and less than 250° C. in water immediately after water-washing the silver-coated particle precursor, for 0.5 to 10 hours.

[Core Particle]

The core particle 2, which is the base body of the silver-coated particle P1, includes spherical particle having a high degree of circularity or irregular particle having a low degree of circularity. The spherical particle may be substantially spherical particles, for example, complete spherical particles, a particle having a shape close to a spherical shape such as an ellipse; and a particle having slight irregularities on the surface. Examples of the irregular particles include rod-like, plate-like, and scale-like particles. The core particle 2 is made of a resin particle or an inorganic particle in terms of material.

Examples of the resin core particle 2 include: the silicone-based resin; the acrylic-based resin; the phenolic-based resin; and the styrene-based resin. These resins are used since they have excellent properties needed in usage of the silver-coated particle P1 as an anisotropic conductive adhesive, a conductive film or the like, such as the way the filler is crushed when load is placed on the filler by weight; and the recovery rate when load is unloaded. Examples of the silicone-based resin include: the silicone resin; the silicone rubber; the silicone resin-coated silicone rubber; and the like. Examples of the acrylic-based resin include: the methyl methacrylate resin (PMMA resin); the acrylic styrene copolymer resin (AS resin); the modified acrylic resin; and the like. Examples of the phenolic-based resin include: the phenol resin; the phenol-formaldehyde resin; the phenol-furfural resin; and the like. Examples of the styrene-based resin include the polystyrene resin; the styrene-acrylonitrile copolymer; the acrylonitrile-butadiene-styrene copolymer resin (ABS resin); and the like. Examples of the inorganic core particle 2 include: talc (talcum); silica; mica; alumina; or boron nitride.

The average particle size of the core particles 2 is desirably in the range of 0.5 to 40 μm. When the average particle size of the core particle 2 is less than 0.5 μm, the surface area of the core particle 2 becomes large, and it is necessary to increase the amount of silver for obtaining the necessary conductivity as the conductive filler or the conductive particle. If the average particle size of the core particle 2 is larger than 40 μm, it becomes difficult to apply the silver-coated particle P1 to a fine pattern.

The average particle diameter of the core particle 2 is measured by software (product name: PC SEM) using a scanning electron microscope (model number: S-4300 SE) manufactured by Hitachi High-Technologies Corporation at a magnification of 2000 times; and the particle sizes of 300 core particles 2 are measured. The average value of the measured values is calculated to obtain the average particle size. In the core particle 2 having a shape other than the true sphere, the value obtained by averaging the long sides is referred to as the average particle diameter.

[Method of Forming the Silver Coating Layer by Electroless Silver Plating/Method of Producing the Silver-Coated Particle Precursor]

On the surface of the core particle 2, the silver coating layer 1 is provided. Generally, when performing electroless plating on the surface of a nonconductor such as an organic material or an inorganic material, it is necessary to perform a catalyzing treatment on the surface of the nonconductor in advance. In the present embodiment, as the catalyzing treatment, a treatment for providing a tin adsorption layer on the surface of the core particle 2 is performed, and then the electroless silver plating treatment is performed to form the silver coating layer 1. Specifically, the silver coating layer 1 of the present embodiment is formed by adding core particles 2 to an aqueous solution of a tin compound kept at 25 to 45° C. to form the tin adsorption layer on the surface of the core particle 2. The tin adsorption layer is formed on the surface of the core particle 2 by electroless silver plating using a reducing agent. In the present specification, one in which the silver coating layer 1 is formed on the surface of the core particle 2 by electroless silver plating is referred to as the silver-coated particle precursor; and the product obtained by heat treatment of this precursor is referred to as the silver-coated particle P1.

In order to form the tin adsorption layer, the core particle 2 is added to the aqueous solution of the tin compound and stirred; the core particle 2 is filtered and washed with water. The stirring time is appropriately determined depending on the temperature of the aqueous solution of the tin compound and the content of the tin compound as described below. Preferable stirring time is 0.5 to 24 hours. The temperature of the aqueous solution of the tin compound is preferably 25 to 45° C. When the temperature of the aqueous solution of the tin compound is less than 25° C., the temperature is too low to lower the activity of the aqueous solution, and the tin compound does not sufficiently adhere to the core particle 2. On the other hand, when the temperature of the aqueous solution of the tin compound exceeds 45° C., the tin compound is oxidized, so that the aqueous solution becomes unstable and the tin compound does not sufficiently adhere to the core particle 2. When this treatment is carried out in an aqueous solution at 25 to 45° C., divalent ions of tin adhere to the surface of the core particle 2 and the tin adsorption layer is formed.

Examples of the tin compound include: stannous chloride; stannous fluoride; stannous bromide; stannous iodide; and the like. When the tin compound is used, the content of tin in the aqueous solution is preferably 20 $g/dm^3$ or more, and can be contained in the aqueous solution until the saturated concentration is reached. In order to improve the solubility of the tin compound, it is preferable to contain 0.8 $cm^3$ or more of hydrochloric acid with respect to 1 g of tin in the aqueous solution.

After the tin adsorption layer is formed on the surface of the core particle 2, electroless silver plating is performed on the tin adsorption layer using a reducing agent to form the silver coating layer 1 on the surface of the core particle 2 to obtain the silver-coated particle precursor. The electroless silver plating method includes: (1) a method in which the core particle 2 with a tin absorbing layer formed on the surface is immersed in an aqueous solution including a complexing agent, a reducing agent and the like, and a silver salt solution is added dropwise to the solution; (TI) a method in which the core particle 2 with a tin absorbing layer formed on the surface is immersed in an aqueous solution including a silver salt and a complexing agent, and an aqueous solution of a reducing agent is added dropwise to the solution; (III) a method in which the core particle 2 with a tin absorbing layer formed on the surface is immersed in an aqueous solution including a silver salt, a complexing agent, a reducing agent and the like, and a caustic alkali solution is added dropwise to the solution.

As the silver salt, silver nitrate or silver nitrate dissolved in nitric acid or the like can be used. As the complexing agent, salts such as: ammonia; ethylenediaminetetraacetic acid; tetrasodium ethylenediaminetetraacetate; nitro triacetic acid; triethylenetetraammine hexacetic acid; sodium thiosulfate; succinate; succinimide; citrate; and iodide salt can be used. As the reducing agent: formalin; glucose;

imidazole; Rochelle salt (sodium potassium tartrate); hydrazine and its derivatives; hydroquinone; L-ascorbic acid; formic acid; and the like can be used. From the strength of reducing power, formaldehyde is preferable as the reducing agent, and a mixture of two or more reducing agents containing at least formaldehyde is more preferable. A mixture of reducing agents containing formaldehyde and glucose is most preferable.

In the electroless silver plating treatment process, a substitution reaction of tin and silver ions in the tin adsorption layer is initiated, and metallic silver serving as a nucleus is precipitated on the surface of the core particle 2. By the above substitution reaction and autocatalytic reduction reaction, the silver coating layer having a predetermined crystallite diameter is formed on the surface of the core particle 2, and a silver-coated particle precursor is obtained.

[Heat Treatment of the Silver-Coated Particle Precursor/Production of the Silver-Coated Particle]

The obtained silver-coated particle precursor is washed with water and dried, and then subjected to heat treatment in the air at a temperature of from 100° C. to less than 250° C. for 0.5 to 10 hours. Alternatively, immediately after washing with water, the obtained silver-coated particle precursor is subjected to heat treatment in water at a temperature of 100° C. to less than 250° C. for 0.5 to 10 hours. By performing one of the heat treatments described above, the silver-coated particle P1 is produced. Specifically, water washing is repeated until the silver-coated particle precursor is decanted in ion exchanged water and the removal of supernatant water is conducted until the electric conductivity becomes 10 μS/cm or less. Drying is carried out by placing the water-washed silver-coated particle precursor in a container such as a stainless vat and maintaining the temperature at 50 to 80° C. using a vacuum dryer. In the case of heat treatment in the air, the dried silver-coated particle precursor is placed in a container similar to that at the time of drying, and the thickness of the bulk is set to 1 cm or less in an air dryer or an electric muffle furnace in the air at a temperature of 100° C. or more and less than 250° C. for 0.5 to 10 hours. In the case of heat treatment in water, the silver-coated particle precursor before drying is suspended in ion exchanged water to be 1 to 20% by mass, and this suspension is stirred at a rotation speed of 100 to 300 rpm in an autoclave, while retaining it at a temperature of 100° C. or higher and less than 250° C. for 0.5 to 10 hours. Preferably, after filtering the suspension, the cake obtained by filtering the suspension is dried at a temperature of 50° C. to 80° C. using a vacuum dryer. Treatment in the air has the advantage that processing can be carried out easily without requiring special equipment; and treatment in water has the advantage that uniform heat treatment is possible. In addition to this, facilities are necessary, but heat treatment may be performed in the air using an apparatus such as an air current dryer or a spray dryer. By this heat treatment, the silver crystallites of the silver coating layer 1 are sintered. This increases the crystallite diameter of silver and increases its crystallinity.

When the heat treatment temperature is less than 100° C. and the heat treatment time is less than 0.5 hour, the silver of the silver coating layer 1 does not thermally diffuse, and sintering hardly occurs, so crystallinity is low. When the heat treatment temperature exceeds 250° C. or more or the heat treatment time exceeds 10 hours, problems occur, such as: peeling of the silver coating layer 1 due to thermal stress between the silver coating layer 1 and the core particles; and progress of aggregation of silver accompanying the peeling. The preferable heat treatment temperature is 120° C. to 200° C., and the heat treatment time is 1 to 5 hours. By changing the heat treatment temperature and/or time within the above range, the size of the crystallite diameter of silver of the silver coating layer 1 can be controlled to fall within the range of 35 nm to 200 nm. Specifically, as the heat treatment temperature is raised or the heat treatment time is lengthened, the silver of the silver coating layer 1 is sintered and the crystallite diameter of silver is increased. As the heat treatment temperature is lowered, or the heat treatment time is shortened, progress of sintering of the silver of the silver coating layer is slowed down; and the crystallite diameter of the silver becomes smaller.

The amount of silver contained in the silver coating layer 1 formed on the surface of the silver-coated particle P1 is 5 to 90 parts by mass with respect to 100 parts by mass of the silver-coated particle. The coating amount (content) of silver is determined by the average particle diameter of the resin and required conductivity. If the silver content is less than 5 parts by mass with respect to 100 parts by mass of the silver-coated particle, the silver coating layer 1 does not cover the core particles 2 with no gap even when the above-described heat treatment is performed. Accordingly, it becomes hard to get contact points between silvers; and impossible to obtain a sufficient conductivity when the silver-coated particles P1 are dispersed as a conductive filler or a conductive particle. On the other hand, when the content of silver exceeds 90 parts by mass, the specific gravity increases, the cost increases, and the conductivity becomes saturated. The content of silver is preferably 28 to 80 parts by mass, more preferably 28 to 70 parts by mass.

[The Conductive Adhesive, the Conductive Film, and the Conductive Spacer]

The silver-coated particles P1 of the present embodiment are excellent as conductive fillers or conductive particles, and can be particularly suitably applied to a conductive adhesive, a conductive film or a conductive spacer.

[Conductive Adhesive]

The conductive adhesive is classified into an isotropic conductive adhesive (ICA: Isotropic Conductive Adhesive) and anisotropic conductive adhesive (ACA: Anisotropic Conductive Adhesive). Further, it has a paste-like, film-like, ink-like form depending on the form of the binder. In the isotropic conductive adhesive, when the binder is cured, the binder shrinks so that the fillers come into contact with each other in the longitudinal direction, the lateral direction, and the oblique direction. Accordingly, the conductive material to be connected is connected to the fillers; and conductivity is obtained. It is also possible to form a sheet with an isotropic conductive adhesive. In an anisotropic conductive adhesive, filler are dispersed in a binder, and an anisotropic conductive adhesive is sandwiched between conductive materials desired to be connected. By pressurizing this in the longitudinal direction, the filler between the conductive materials to be connected and the conductive material to be connected are in contact in the longitudinal direction to obtain conductivity. On the other hand, since the fillers are arranged in the transverse direction via the binder which is an insulator, the portions not pressed are not in contact with each other, so that conductivity cannot be obtained.

Examples of the conductive adhesive include: the anisotropic or isotropic conductive paste; the anisotropic or isotropic conductive ink; and the like. The conductive adhesive is prepared by uniformly mixing the conductive particles comprising the silver-coated particles P1 of the present embodiment and the insulating binder resin using a kneading machine such as a planetary mixer or a triple roll mill. In the conductive adhesive, the conductive particles are uniformly dispersed in the insulating binder resin. The content of the silver-coated particles P1 is not particularly limited and may be appropriately determined depending on the application and the like, but is preferably in the range of 0.5 part to 5 parts by mass with respect to 100 parts by mass of the binder resin.

The insulating binder resin in the conductive adhesive is not particularly limited, and examples thereof include: the thermoplastic resin; the composition of a curable resin composition curable by heat or light; and the like. Examples of the thermoplastic resin include: the styrene-butadiene block copolymer; the acrylate resin; the ethylene-vinyl acetate resin; and the like. The curable resin composition includes a resin composition containing: an epoxy type monomer or oligomer having a glycidyl group; and a curing agent such as isocyanate.

[Conductive Film]

As the conductive film, there is an anisotropic or isotropic conductive film formed into a film shape. The conductive film is produced by: first preparing the resin composition in which the conductive particles made of the silver-coated particle P1 of the present embodiment are dispersed in the insulating binder resin; and then by applying the resin composition on the surface of the support film such as PET or the like. This resin composition is prepared by uniformly mixing the conductive particles and the insulating binder resin using a kneading machine such as a planetary mixer or a triple roll mill. In the conductive film, the conductive particles are uniformly dispersed in the insulating binder resin on the support film. The insulating binder resin in the conductive film includes a resin composition containing a thermosetting resin such as an epoxy resin; a phenoxy resin; or the like, as a main component. The content of the silver-coated particles P1 in the resin composition in the conductive film is not particularly limited and may be appropriately determined depending on the application and the like, but is preferably in the range of 0.5 to 10 parts by mass with respect to 100 parts by mass of the binder resin.

[Conductive Spacer]

The conductive spacer is used in a liquid crystal display device by electrically connecting upper and lower wiring portions of upper and lower substrates sandwiching a liquid crystal substance therebetween and maintaining a gap between the substrates at a predetermined dimension. The conductive space is produced by: first preparing the mixture of the conductive particles and the binder resin by mixing them uniformly by using a kneading machine such as a planetary mixer or a triple roll mill after adding the conductive particles made of the silver-coated particle P1 of the present embodiment to the insulating binder resin such as a thermosetting resin or an ultraviolet curable adhesive; then applying the above-described resin composition on one or both of wiring portions of the two upper and lower substrates for them to be pasted each other. The content of the silver-coated particles P1 is not particularly limited and may be appropriately determined depending on the use and the like, but it is preferably in the range of 2 to 10 parts by mass based on 100 parts by mass of the binder resin.

In the conductive adhesive, the conductive film, or the conductive spacer including the conductive particles including the silver-coated particles P1 of the present embodiment, cracking or fracturing of the silver coating layer 1 or peeling of the silver coating layer 1 from the core particle 2 hardly occurs; and the conductivity is improved further, even if a high shear force is applied in kneading of the mixture of the conductive particles and the insulating binder resin. Thus, when the silver-coated particle P1 of the present invention is used, for example, as an anisotropic conductive adhesive, it is possible to avoid a short circuit in the anisotropic conduction (lateral direction), thereby improving the reliability.

EXAMPLES

Next, Examples of the present invention will be described in detail together with Comparative Examples.

Example 1

Firstly, 20 g of stannous chloride and 15 $cm^3$ of hydrochloric acid having a concentration of 35% were diluted (scalpel) to 1 $dm^3$ with water using a volumetric flask having a capacity of 1 $dm^3$ and kept at 30° C. To this aqueous solution, 50 g of a spherical acrylic-styrene copolymer resin having the average particle size of 10 μm was added as a core particle serving as the matrix and stirred for 1 hour. Thereafter, the pre-treatment was performed by separating the acrylic styrene copolymer resin by filtration and water-washing the separated acrylic styrene copolymer resin.

Next, on the surface of the acrylic styrene copolymer resin having the tin adsorption layer formed on the surface by the pretreatment, a silver coating layer was formed by electroless plating. Specifically, first, 40 g of sodium ethylenediaminetetraacetate as a complexing agent, 20.0 g of sodium hydroxide as a pH adjusting agent and 15 ml of formalin (formaldehyde concentration 37 mass %) as a reducing agent were added to 2 $dm^3$ of water to prepare an aqueous solution containing a complexing agent and a reducing agent. Next, slurry was prepared by immersing the pre-treated acrylic styrene copolymer resin in this aqueous solution.

Then, 30 g of silver nitrate, 35 ml of 25% aqueous ammonia and 50 ml of water were mixed to prepare an aqueous solution containing silver nitrate. The aqueous solution containing silver nitrate was added dropwise to the slurry while stirring the slurry. Then, silver was precipitated on the surface of the resin by: adjusting pH of the slurry to 12 by adding hydroxide solution to the slurry dropwise sodium; and stirring it while the temperature was kept at 25° C. Thereafter, washing and filtration were conducted, and finally dried at a temperature of 60° C. using a vacuum dryer to obtain a silver-coated particle precursor. Then, the silver-coated particle having silver at the amount of 45 mass % with respect to 100 mass % of the silver-coated particle was obtained by spreading the silver-coated particle precursors on a stainless steel vat so as to be in 1 mm of the thickness after loosening the agglomerated particles in the silver-coated particle precursors by using a 325 mesh stainless steel plain weave wire mesh and an oscillating sieve; heat treating by holding them at 140° C. for 4 hours after increasing temperature to 140° C. in 30 minutes in the electric muffle furnace; and sintering the crystallites of silver in the silver coating layer.

Example 2

A spherical acrylic styrene copolymer resin having the average particle diameter of 3 μm was used as the core particle to form the base body, and the mass of silver to be plated was adjusted. The temperature during the heat treatment was 150° C., and the holding time was 3 hours. Other than that, silver-coated particles having the amount of silver of 65% by mass with respect to 100% by mass of silver-coated particles were obtained in the same manner as in Example 1. The silver-coated particles were solidified with epoxy resin and sliced, and then observed with TEM (Transmission Electron Microscope). FIG. 1 shows a TEM image (magnification of 500,000 times) of the silver coated layer cross section of the silver-coated particles. In FIG. 1, the inside of the silver coating layer 1 is the core particle 2 to be the base body and the outside of the silver coating layer is the solidified resin 3.

Example 3

Spherical acrylic styrene copolymer resin having the average particle size of 1 µm was used as the core particle to be the base body, and the mass of silver to be plated was adjusted. The temperature during the heat treatment was 120° C., and the holding time was 7 hours. Other than that, silver-coated particles having the amount of silver of 90% by mass with respect to 100% by mass of silver-coated particles were obtained in the same manner as in Example 1.

Example 4

The procedure of Example 1 was repeated except that the mass of silver to be plated was adjusted using the spherical acrylic styrene copolymer resin having the average particle size of 20 µm as the core particles as the base body. In the same manner, silver-coated particles having the amount of silver of 25% by mass with respect to 100% by mass of silver-coated particles were obtained.

Example 5

Spherical acrylic styrene copolymer resin having the average particle size of 40 µm was used as the core particle to be the base body, and the mass of silver to be plated was adjusted. The temperature during the heat treatment was 160° C., and the holding time was 1.5 hours. Other than that, silver-coated particles having the amount of silver of 15% by mass with respect to 100% by mass of silver-coated particles were obtained in the same manner as in Example 1.

Example 6

The mass of silver to be plated was adjusted by using the same acrylic styrene copolymer resin as in Example 1 as the core particle to be the base body. The temperature during the heat treatment was 130° C., and the holding time was 4 hours. Other than that, the same procedure as in Example 1 was carried out to obtain silver-coated particles having the amount of silver of 20% by mass with respect to 100% by mass of silver-coated particles.

Example 7

The mass of silver to be plated was adjusted by using the same acrylic styrene copolymer resin as in Example 1 as the core particle to be the base body. The temperature during the heat treatment was 160° C., and the holding time was 6 hours. Other than that, silver-coated particles having the amount of silver of 80% by mass with respect to 100% by mass of silver-coated particles were obtained in the same manner as in Example 1.

Example 8

The mass of silver to be plated was adjusted by using the same acrylic styrene copolymer resin as in Example 5 as the core particle to be the base body. Other than that, in the same manner as in Example 5, silver-coated particles having the amount of silver of 5% by mass with respect to 100% by mass of silver-coated particles were obtained.

Example 9

The same acrylic styrene copolymer resin as in Example 1 was used as the core particle to be the base body. Heat treatment in the air of Example 1 was carried out at 100° C. Other than that, the same procedure as in Example 1 was carried out to obtain silver-coated particles having the amount of silver of 45% by mass with respect to 100% by mass of the silver-coated particles.

Example 10

The same acrylic styrene copolymer resin as in Example 1 was used as the core particle to be the base body. Heat treatment in the air of Example 1 was carried out at 200° C. Other than that, the same procedure as in Example 1 was carried out to obtain silver-coated particles having the amount of silver of 45% by mass with respect to 100% by mass of the silver-coated particles.

Example 11

The same acrylic styrene copolymer resin as in Example 1 was used as the core particle to be the base body. Heat treatment in the air of Example 1 was carried out for 0.5 hour. Other than that, the same procedure as in Example 1 was carried out to obtain silver-coated particles having the amount of silver of 45% by mass with respect to 100% by mass of the silver-coated particles.

Example 12

The same acrylic styrene copolymer resin as in Example 1 was used as the core particle to be the base body. Heat treatment in the air of Example 1 was carried out for 10 hours. Other than that, the same procedure as in Example 1 was carried out to obtain silver-coated particles having the amount of silver of 45% by mass with respect to 100% by mass of the silver-coated particles.

Example 13

The same acrylic styrene copolymer resin as in Example 1 was used as the core particle to be the base body. A silver-coated particle precursor was obtained in the same manner as in Example 1 except that the drying of Example 1 was not carried out. The obtained silver-coated particle precursor was heat-treated in water. Specifically, the silver-coated particle precursor was suspended in ion-exchanged water to be 10% by mass, and then the suspension was stirred at the rotation speed of 150 rpm in an autoclave at a temperature of 150° C. After holding for 3 hours and heat treating to sinter the silver crystallites of the silver coating layer, the cake obtained by filtering the suspension was dried at a temperature of 60° C. using a vacuum dryer. As a result, silver-coated particles having the amount of silver of 45% by mass with respect to 100% by mass of silver-coated particles were obtained.

Example 14

A spherical phenol resin having the average particle diameter of 10 µm was used as the core particle to be the base body, and the temperature during heat treatment was 160° C., and the holding time was 1 hour. Other than that, the same procedure as in Example 1 was carried out to obtain silver-coated particles having the amount of silver of 45% by mass with respect to 100% by mass of the silver-coated particles.

Example 15

A spherical polystyrene resin having the average particle size of 10 µm was used as the core particle to be the base body, and the temperature during the heat treatment was 120° C. and the holding time was 8 hours. Other than that, the same procedure as in Example 1 was carried out to obtain silver-coated particles having the amount of silver of 45% by mass with respect to 100% by mass of the silver-coated particles.

Example 16

A spherical silicone resin having the average particle size of 2 µm was used as the core particle to be the base body and the mass of silver to be plated was adjusted. Other than that, silver-coated particles having the amount of silver of 80% by mass with respect to 100% by mass of silver-coated particles were obtained in the same manner as in Example 1.

Example 17

As the core particles to be the base body, the mass of silver to be plated was adjusted by using a rod-like atomized silicone resin having the average particle diameter of 10 µm. The temperature during heat treatment was 130° C., and the holding time was 5 hours. Other than that, the same procedure as in Example 1 was carried out to obtain silver-coated particles having the amount of silver of 50% by mass with respect to 100% by mass of the silver-coated particles.

Example 18

Plate-like boron nitride powder having the average particle diameter of 8 µm was used as the core particle to adjust the mass of silver to be plated. Other than that, in the same manner as in Example 1, silver-coated particles having the amount of silver of 60% by mass with respect to 100% by mass of the silver-coated particles were obtained.

Example 19

A scaly talc powder having the average particle size of 5 µm was used as the core particle to be the base body, and the mass of silver to be plated was adjusted. The temperature during the heat treatment was 150° C., and the holding time was 3 hours. Other than that, in the same manner as in Example 1, silver-coated particles having the amount of silver of 70% by mass with respect to 100% by mass of the silver-coated particles were obtained.

Example 20

Spherical silicone rubber particles having the average particle size of 10 µm were used as core particles to prepare the mass of silver to be plated. The temperature during heat treatment was 245° C., and the holding time was 1 hour. Other than that, in the same manner as in Example 1, silver-coated particles having the amount of silver of 45% by mass with respect to 100% by mass of the silver-coated particles were obtained.

Comparative Example 1

The same acrylic styrene copolymer resin as in Example 1 was used as the core particle to be the base body. A silver-coated particle precursor was obtained in the same manner as in Example 1. The silver-coated particle precursor obtained was not heat treated. By following the above-described procedure, silver-coated particles having the amount of silver of 45% by mass with respect to 100% by mass of the silver-coated particles were obtained.

Comparative Example 2

Figure 2:
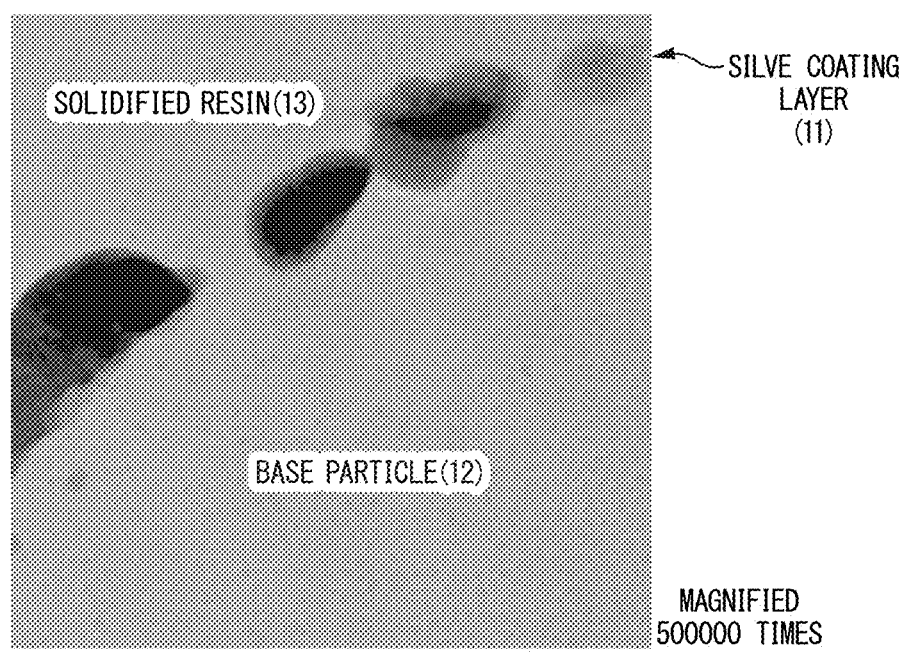
FIG. 2 shows a TEM image (magnification of 500,000 times) of a cross section of a silver coating layer of silver-coated particles P2 of Comparative Example 2. The core particle 12 and the silver coating layer 11 of the silver-coated particle P2 of the Comparative Example are shown with the solidified resin 13.

The same acrylic styrene copolymer resin as in Example 2 was used as the core particle to be the base body. A silver-coated particle precursor was obtained in the same manner as in Example 2. The silver-coated particle precursor obtained was not heat treated. By following the above-described procedure, silver-coated particles having the amount of silver of 65% by mass with respect to 100% by mass of the silver-coated particles were obtained. As in Example 2, the silver-coated particles were hardened with epoxy resin, sliced, and then observed with TEM. FIG. 2 shows a TEM image (magnification of 500,000 times) of the silver coated layer cross section of the silver-coated particle P2. In FIG. 2, the inside of the silver coating layer 11 is the core particle 12 to be the base body and the outside of the silver coating layer is the solidified resin 13.

Comparative Example 3

The same acrylic styrene copolymer resin as in Example 1 was used as the core particle to be the base body. Heat treatment in the air of Example 1 was carried out for 0.25 hour. Other than that, silver-coated particles having the amount of silver of 45% by mass with respect to 100% by mass of silver-coated particles were obtained in the same manner as in Example 1.

Comparative Example 4

The same acrylic styrene copolymer resin as in Example 1 was used as the core particle to be the base body. Heat treatment in the air of Example 1 was conducted for 11 hours. Other than that, silver-coated particles having the amount of silver of 45% by mass with respect to 100% by mass of silver-coated particles were obtained in the same manner as in Example 1.

Comparative Example 5

The same acrylic styrene copolymer resin as in Example 1 was used as the core particle to be the base body. Heat treatment in the air of Example 1 was carried out at 90° C. Other than that, silver-coated particles having the amount of silver of 45% by mass with respect to 100% by mass of silver-coated particles were obtained in the same manner as in Example 1.

Comparative Example 6

The same acrylic styrene copolymer resin as in Example 1 was used as the core particle to be the base body. Heat treatment in the air of Example 1 was carried out at 255° C. Other than that, silver-coated particles having the amount of silver of 45% by mass with respect to 100% by mass of silver-coated particles were obtained in the same manner as in Example 1.

Comparative Example 7

A scaly talc powder having the average particle diameter of 3 μm was used as a core particle to be the base material, and the mass of silver to be plated was adjusted. Other than that, in the same manner as in Example 1, the silver-coated particle precursor was obtained. The silver-coated particle precursor obtained was not heat treated. By following the procedure described above, silver-coated particles having the amount of silver of 78% by mass with respect to 100% by mass of the silver-coated particles were obtained.

Table 1 shows the material of the core particles, the average particle diameter, the amount of silver in the silver-coated particles, the heat treatment atmosphere during the production of the silver-coated particles, the heat treatment temperature and the heat treatment time in Examples 1 to 19 and Comparative Examples 1 to 7. In Table 1, "AS resin" means "acrylic-styrene copolymer resin."

[Comparative Test and Evaluation]

With respect to the silver-coated particles obtained in Examples 1 to 20 and Comparative Examples 1 to 7, each of the average film thickness of the silver coating layer; the crystallite diameter of silver of the silver coating layer; the appearance of the silver coating layer before and after application of the shear stress; and the resistance of the silver-coated particle before and after application of the shear stress of 20% compression, was evaluated by the methods described below. These results are shown in Table 2.

(1) Average Film Thickness of the Silver Coating Layer

The average film thickness of the silver coating layer was determined from the formula indicated below, wherein d is the average film thickness; r is the value that the average grain size the core particles is divided by 2; $d_{core}$ is the density of the core particle; and a is the mass ratio of the mass of the silver in the silver-coated particle to the mass of the silver-coated particle.

TABLE 1

| | Material and physical properties of the core particle | | | Amount of silver in the silver-coated particle (mass %) | Heat treatment condition | | |
|---|---|---|---|---|---|---|---|
| | Material | Average particle diameter (μm) | Shape of the particle | | Atmosphere | Temperature (° C.) | Time (hour) |
| Example 1 | AS resin | 10 | Spherical | 45 | In the air | 140 | 4 |
| Example 2 | AS resin | 3 | Spherical | 65 | In the air | 150 | 3 |
| Example 3 | AS resin | 1 | Spherical | 90 | In the air | 120 | 7 |
| Example 4 | AS resin | 20 | Spherical | 25 | In the air | 150 | 3 |
| Example 5 | AS resin | 40 | Spherical | 15 | In the air | 160 | 1.5 |
| Example 6 | AS resin | 10 | Spherical | 20 | In the air | 130 | 4 |
| Example 7 | AS resin | 10 | Spherical | 80 | In the air | 160 | 6 |
| Example 8 | AS resin | 40 | Spherical | 5 | In the air | 150 | 3 |
| Example 9 | AS resin | 10 | Spherical | 45 | In the air | 100 | 3 |
| Example 10 | AS resin | 10 | Spherical | 45 | In the air | 200 | 3 |
| Example 11 | AS resin | 10 | Spherical | 45 | In the air | 150 | 0.5 |
| Example 12 | AS resin | 10 | Spherical | 45 | In the air | 150 | 10 |
| Example 13 | AS resin | 10 | Spherical | 45 | In water | 150 | 3 |
| Example 14 | Phenol resin | 10 | Spherical | 45 | In the air | 160 | 2 |
| Example 15 | Polystyrene resin | 10 | Spherical | 45 | In the air | 120 | 8 |
| Example 16 | Silicone resin | 2 | Spherical | 80 | In the air | 140 | 4 |
| Example 17 | Silicone resin | 10 | Spherical | 50 | In the air | 130 | 5 |
| Example 18 | Boron nitride | 8 | Spherical | 60 | In the air | 140 | 4 |
| Example 19 | Talc | 5 | Scaly | 70 | In the air | 150 | 3 |
| Example 20 | Silicone rubber | 10 | Spherical | 45 | In the air | 245 | 1 |
| Comparative Example 1 | AS resin | 10 | Spherical | 45 | — | — | — |
| Comparative Example 2 | AS resin | 3 | Spherical | 65 | — | — | — |
| Comparative Example 3 | AS resin | 10 | Spherical | 45 | In the air | 150 | 0.25 |
| Comparative Example 4 | AS resin | 10 | Spherical | 45 | In the air | 150 | 11 |
| Comparative Example 5 | AS resin | 10 | Spherical | 45 | In the air | 90 | 3 |
| Comparative Example 6 | AS resin | 10 | Spherical | 45 | In the air | 255 | 3 |
| Comparative Example 7 | Talc | 3 | Scaly | 78 | — | — | — |

$$d = r\left\{\left(\frac{ad_{core}}{(1-a)d_{Ag}} + 1\right)^{\frac{1}{3}} - 1\right\}$$ [Formula 1]

2) Silver Crystallite Diameter of the Silver Coating Layer

The crystallite diameter of the silver in the silver coating layer was determined by filling the sample with the silver halide emulsion in the sample holder attached to the X-ray diffraction apparatus and irradiating X-rays in a range of 2θ/θ=30 to 120 deg. In this embodiment, the crystallite diameter of the silver of the silver coating layer was measured by using an X-ray diffractometer Empyrean manufactured by PANalytical Co., Ltd., filling the obtained powdery silver-coated particles in the sample holder attached to this device. Then, X-rays were irradiated in the range of 2θ/θ=30 to 120 deg. The obtained diffraction line was analyzed by the Pawley method using FP as the profile function using the analysis software TOPAS (manufactured by Bruker AXS); and the crystallite diameter was calculated from the half width of the Lorentz function component. Measurement was carried out using Cu bulbs at 40 kV and 40 mA, with characteristic X-rays (wavelength 1.54 Å) and the step interval of 0.025 deg. From the analysis by this Pawley method, the crystallite diameter of silver of the silver coating layer was obtained. As a reference method for measuring the crystallite diameter of silver, there is the method using Scherrer's equation. This method is a method used for measuring the crystallite diameter of silver in the aforementioned PTL 2 (see paragraph [0021]). In this method, the average value of the crystallite diameter in the (111) plane, the (200) plane, the (220) plane and the (311) plane of the silver crystal is calculated as the value of the crystallite diameter. The Scherrer's equation is: $D_{hkl}=K\lambda/\beta \cos \theta$ (where $D_{hkl}$ is the crystallite diameter (m), λ is the measured X-ray wavelength (m), K is a constant=0.9, β is the half width (rad), and θ is the Bragg angle (rad) of the diffraction line. In terms of the relationship between the measured value based on the measurement method in the present invention and one based on the reference Scherrer's equation, "the range of the crystallite diameter of 18 to 24 nm" described in the claim 1 of PTL 2 corresponds to "the range of the crystallite diameter of 26 to 34 nm" obtained based on the measurement method in the present invention.

(3) Appearance Evaluation of the Silver Coating Layer Before and after Application of Shear Stress Shear stress test was conducted by the following method described below. Eighty parts by mass of the silver-coated particles were made into a paste-like mixture by using 20 parts by mass of ethylene glycol and a planetary mixer (Awatori rentaro manufactured by Thinky Co., Ltd.). This paste-like mixture was kneaded ten times with a three-roll mill (EXACT M-80E) to apply shear stress to the silver-coated particles. The rotational speeds of the three rolls at this time were set to 30 rpm, 55 rpm, 100 rpm, and the interval between the rolls was set to a value five times the particle diameter of silver-coated particles. Before and after applying the shear stress to silver-coated particles, the appearance of silver-coated particles was observed and evaluated by a scanning electron microscope (model number: S-4300SE) manufactured by Hitachi High-Technologies Corporation. At this time, the appearance "A" was defined as the state where silver-coated particles having crack and fracture; or peeling of the silver coating layer from the core particle were present in the amount of 5% or less of the total. The appearance "13" was defined as the state where silver-coated particles having crack and fracture; or peeling of the silver coating layer from the core particles were present in the amount of 5 to 20% of the total. The appearance "C" was defined as the state where silver-coated particles having crack and fracture; or peeling of the silver coating layer from the core particles were present in the amount of 20 to 100% of the total.

(4) Resistance of the Silver-Coated Particle Before and after Application of Shear Stress by Compression Shear stress test was performed on silver-coated particles by the method in (3) described above. Before and after the shear stress test, compression test of silver-coated particles was carried out. This compression test was carried out in the state where one silver-coated particle was compressed in the vertical direction using a micro compression tester (MCT-W 200 J manufactured by Shimadzu Corporation). The compression ratio was 20% in the case of spherical particles and 5% in the case of particles with aspect ratio of 2 or more on the long side and short side of the plate-like particles. The electric resistance value of silver-coated particles when compressed was measured by energizing with the same apparatus. The average of the resistance values when 10 silver-coated particles were measured for one condition was taken as the measurement value.

TABLE 2

| | Silver coating layer | | Appearance of the silver coating layer before and after application of the shear stress | | Resistance value of the silver-coated particle before and after application of the shear stress | |
|---|---|---|---|---|---|---|
| | Average film thickness (nm) | Crystallite diameter of silver (nm) | Before | After | Before (Ω) | After (Ω) |
| Example 1 | 150 | 70 | A | A | 50 | 58 |
| Example 2 | 150 | 64 | A | A | 80 | 79 |
| Example 3 | 145 | 53 | A | A | 92 | 98 |
| Example 4 | 150 | 72 | A | A | 42 | 45 |
| Example 5 | 150 | 80 | A | A | 38 | 42 |
| Example 6 | 50 | 35 | A | A | 96 | 104 |
| Example 7 | 1000 | 200 | A | A | 12 | 15 |
| Example 8 | 50 | 37 | A | A | 102 | 114 |
| Example 9 | 150 | 38 | A | A | 56 | 89 |
| Example 10 | 150 | 118 | A | A | 66 | 64 |
| Example 11 | 150 | 36 | A | A | 54 | 88 |

TABLE 2-continued

| | Silver coating layer | | Appearance of the silver coating layer before and after application of the shear stress | | Resistance value of the silver-coated particle before and after application of the shear stress | |
|---|---|---|---|---|---|---|
| | Average film thickness (nm) | Crystallite diameter of silver (nm) | Before | After | Before (Ω) | After (Ω) |
| Example 12 | 150 | 126 | A | A | 49 | 57 |
| Example 13 | 150 | 76 | A | A | 72 | 80 |
| Example 14 | 150 | 72 | A | A | 52 | 56 |
| Example 15 | 150 | 75 | A | A | 42 | 45 |
| Example 16 | 150 | 55 | A | A | 71 | 75 |
| Example 17 | 160 | 72 | A | A | 81 | 86 |
| Example 18 | 150 | 55 | A | A | 71 | 75 |
| Example 19 | 300 | 128 | A | A | 110 | 122 |
| Example 20 | 140 | 106 | A | A | 41 | 42 |
| Comparative Example 1 | 150 | 32 | A | C | 58 | 1000 or more |
| Comparative Example 2 | 150 | 29 | A | C | 78 | 1000 or more |
| Comparative Example 3 | 50 | 33 | A | B | 62 | 512 |
| Comparative Example 4 | 500 | 206 | B | B | 215 | 820 |
| Comparative Example 5 | 150 | 22 | A | C | 60 | 1000 or more |
| Comparative Example 6 | 150 | 95 | C | C | 1000 or more | 1000 or more |
| Comparative Example 7 | 700 | 192 | A | C | 21 | 1000 or more |

As is apparent from Table 2, with respect to the silver-coated particles of Examples 1 to 2; Examples 4 to 5; and Examples 13 to 18 in which the crystallite diameter was controlled by applying an appropriate heat treatment, there was almost no change in the appearance and the resistance value at the time of compression. Thus, the silver-coated particles suitable for applications such as conductive adhesive and conductive spacer were obtained. In addition, with respect to Example 3, in which the amount of silver in the silver-coated particles was set to the upper limit value, although the cost increased due to the increase in the amount of silver, there was almost no change in the appearance and the resistance value at the time of compression as in Examples described above, the silver-coated particles suitable for applications such as conductive adhesive and conductive spacer were obtained.

In Example 6 in which the crystallite diameter of silver was set to the lower limit value of the crystallite diameter of the silver; and Example 7 in which the crystallite diameter of the silver was set to the upper limit value, although there was a slight change in the resistance value before and after application of the shear stress at the time of compression, excellent silver-coated particles with good appearance were obtained.

In Example 8 in which the amount of silver of the silver-coated particles reached the lower limit value, the initial resistance value was slightly high, but the change before and after application of the shear stress was small; and excellent silver-coated particles with good appearance were obtained.

In Example 9 in which the heat treatment temperature was relatively low, and in Example 11 in which the heat treatment time was relatively short, the crystallite diameter became smaller according to the condition of the treatment. In addition, although there was some change in the resistance value before and after application of the shear stress at the time of compression, excellent silver-coated particles with good appearance were obtained.

In Examples 10 and 20 in which the heat treatment temperature was relatively high and in Example 12 in which the heat treatment time was relatively long, although the crystallite diameter greatly increased, excellent silver-coated particles with good appearance and resistance value were obtained.

In Example 19 using talc which was the inorganic material as the core particle, although the resistance value at the time of compression was relatively high, change of the resistance value before and after application of shear stress was small; and excellent silver-coated particles with good appearance were obtained.

On the other hand, in the silver-coated particles of: Comparative Examples 1, 2 and 7 in which the heat treatment was not performed; Comparative Example 3 in which the heat treatment time was less than 0.5 hour; and Comparative Example 5 in which the heat treatment temperature was less than 100° C., the silver was peeled off after application of the shear stress since the crystallite diameter was lower less than 35 nm. Accordingly, the appearance was deteriorated; and the resistance value showed a high value of 1000 or more at the time of compression, making the particles unsuitable as a conductive particle.

In the silver-coated particles of Comparative Example 4 in which the heat treatment time exceeded 10 hours; and Comparative Example 6 in which the heat treatment temperature was 250° C. or higher, the crystallite diameter exceeded 200 nm since the heat treatment time was too long. Accordingly, the silver-coated particles were deformed by shrinkage of the silver-coated layer by being over-sintered; partial peel off of the silver was observed in both before and after application of shear stress for the appearance to be deteriorated; and the resistance values showed high values of 820Ω and 1000Ω, respectively, at the time of compression, making the particles unsuitable as a conductive particle.

From FIG. 1 showing a TEM image (magnification of 500,000 times) of the silver coating layer cross section of the silver-coated particle of Example 2, it is demonstrated that the silver in the silver coating layer was sintered to increase the crystallite diameter, and thereby the silver coating layer covered the core particle without gaps. As a result, the silver coating layer was not peeled off even after application of the shear stress, and a smooth coating layer was retained. On the other hand, from FIG. 2 showing a TEM image (magnification of 500,000 times) of the silver coated layer cross section of the silver-coated particle of Comparative Example 2, it was demonstrated that the silver coating layer did not cover the core particle without gaps since the silver crystallite in the silver coating layer was small. As a result, silver was peeled off due to grain boundary fracture at the time of application of shear stress.

INDUSTRIAL APPLICABILITY

The silver-coated particle of the present invention can be utilized as conductive fillers or conductive particles of an anisotropic or isotropic conductive adhesive, an anisotropic or isotropic conductive film, and an anisotropic or isotropic conductive spacer.

REFERENCE SIGNS LIST

P1: Silver-coated particle
1: Silver coating layer
2: Core particle (Base particle)
3: Solidified resin
P2: Silver-coated particle (Comparative Example)
11: Silver coating layer (Comparative Example)
12: Core particle (Base particle, Comparative Example)
13: Solidified resin (Comparative Example)

The invention claimed is:

1. A silver-coated particle comprising a core particle made of a resin particle or an inorganic particle and a silver coating layer formed on a surface of the core particle by electroless silver plating, wherein,
    an amount of silver contained in the silver coating layer is 25 to 80 parts by mass with respect to 100 parts of the silver-coated particle,
    a crystallite diameter of the silver, which is calculated from a diffraction line obtained by filling a sample holder belonging to an X-ray diffraction apparatus with the silver-coated particle; and irradiating X-ray in a range of 2θ/θ=30 to 120 deg., is in a range of 35 nm to 200 nm,
    the crystallite diameter of the silver is smaller than an average film thickness of the silver coating layer.

2. A method of producing a silver-coated particle comprising the steps of:
    forming a tin absorbing layer on a surface of a core particle at a temperature of 25 to 45° C., for 0.5 to 24 hours by adding the core particle made of a resin particle or an inorganic particle to an aqueous solution of a tin compound;
    preparing a silver-coated particle precursor, which contains a silver coating layer on the surface of the core particle, by performing electroless plating on the tin absorbing layer, which is formed on the surface of the core particle, by using a reducing agent; and
    setting a crystallite diameter of the silver, which is measured by X-ray diffraction method, to 35 nm to 200 nm by sintering silver constituting the silver coating layer by heat treating the silver-coated particle precursor at: a temperature of 100° C. or more and less than 250° C. in an air after water-washing and drying the silver-coated particle precursor; or a temperature of 100° C. or more and less than 250° C. in water immediately after water-washing the silver-coated particle precursor, for 0.5 to 10 hours.

3. A method of producing a conductive adhesive by mixing the silver-coated particle according to claim 1 and a binder resin.

4. A method of producing a conductive film by applying a resin composition, which is prepared by mixing the silver surface-coated particle according to claim 1 and a binder resin, on a surface of a support film.

5. A method of producing a conductive spacer by pasting two substrate plates after applying a resin composition, which is prepared by mixing the silver surface-coated particle according to claim 1 and a binder resin, on one or both surfaces of the two substrate plates.

6. The silver-coated particle according to claim 1, wherein the crystallite diameter of the silver is in a range of 40 nm to 80 nm,
    the silver coating layer coats the core particle with no gap.

7. The method of producing a silver-coated particle according to claim 2, wherein
    the step of sintering silver constituting the silver coating layer sets crystallite diameter of the silver, which is measured by X-ray diffraction method, to 40 nm to 80 nm, and makes the silver coating layer coat the core particle with no gap.

8. The method of producing a silver-coated particle according to claim 2, wherein
    in the case of the heat treatment in water, the silver-coated particle precursor before drying is suspended in ion exchanged water to be 1 to 20% by mass, then the suspension is retained at a temperature of 100° C. or higher and less than 250° C. for 0.5 to 10 hours, the cake obtained by filtering the suspension is dried at a temperature of 50° C. to 80° C. using a vacuum dryer.

9. The method of producing a silver-coated particle according to claim 2, wherein
    the tin compound is selected from stannous chloride, stannous fluoride, stannous bromide, and stannous iodide,
    the content of tin in the aqueous solution of the tin compound is 20 g/dm$^3$ or more,
    the aqueous solution contains 0.8 cm$^3$ or more of hydrochloric acid with respect to 1 g of tin in the aqueous solution.

* * * * *